United States Patent
Lapid (10) Patent No.: US 8,092,485 B2
(45) Date of Patent: Jan. 10, 2012

(54) RECOVERABLE INFERIOR VENA CAVA FILTER

(75) Inventor: Inbal Sarah Lapid, Tempe, AZ (US)

(73) Assignee: C. R. Bard, Inc., Murray Hill, NJ (US)

( * ) Notice: Subject to any disclaimer, the term of this patent is extended or adjusted under 35 U.S.C. 154(b) by 317 days.

(21) Appl. No.: 12/518,701

(22) PCT Filed: Dec. 12, 2007

(86) PCT No.: PCT/US2007/087235
§ 371 (c)(1),
(2), (4) Date: Jun. 11, 2009

(87) PCT Pub. No.: WO2008/073971
PCT Pub. Date: Jun. 19, 2008

(65) Prior Publication Data
US 2010/0016882 A1  Jan. 21, 2010

Related U.S. Application Data

(60) Provisional application No. 60/869,624, filed on Dec. 12, 2006.

(51) Int. Cl.
*A61F 2/01* (2006.01)

(52) U.S. Cl. ........................................... 606/200

(58) Field of Classification Search .................. 606/200, 606/159, 110, 113, 114, 127, 198; 604/19, 604/27, 104–107; 128/830, 831, 843
See application file for complete search history.

(56) References Cited

U.S. PATENT DOCUMENTS

| | | | |
|---|---|---|---|
| 5,370,657 A | 12/1994 | Irie | |
| 5,626,605 A | 5/1997 | Irie et al. | |
| 5,746,767 A * | 5/1998 | Smith | 606/200 |
| 5,836,969 A | 11/1998 | Kim et al. | |
| 6,126,673 A | 10/2000 | Kim et al. | |
| 6,258,026 B1 | 7/2001 | Ravenscroft et al. | |
| 6,273,901 B1 | 8/2001 | Whitcher et al. | |
| 6,589,266 B2 | 7/2003 | Whitcher et al. | |
| 6,793,665 B2 | 9/2004 | McGuckin, Jr. et al. | |
| 7,018,401 B1 | 3/2006 | Hyodoh et al. | |
| 2003/0060843 A1 | 3/2003 | Boucher | |
| 2005/0080447 A1 | 4/2005 | McGuckin, Jr. et al. | |
| 2005/0288703 A1 | 12/2005 | Beyer et al. | |
| 2006/0041271 A1 | 2/2006 | Bosma et al. | |

* cited by examiner

*Primary Examiner* — Elizabeth Houston
(74) *Attorney, Agent, or Firm* — Garvey, Smith, Nehrbass & North, L.L.C.; Seth M. Nehrbass; Charles C. Garvey, Jr.

(57) ABSTRACT

A recoverable embolus filter has a symmetrical design with two corollas with radially extending extensions that are mutually interconnected to permit them to slide with respect to each other. The corollas collapse by pulling them apart, and the collapsed filter can then be withdrawn by pulling one of the ends of the collapsed configuration into a recovery sheath.

19 Claims, 10 Drawing Sheets

RECOVERABLE INFERIOR VENA CAVA FILTER

PRIORITY DATA AND INCORPORATION BY REFERENCE

This application claims the benefit of priority to U.S. Provisional Patent Application No. 60/869,624, filed Dec. 12, 2006, which is incorporated by reference in its entirety.

TECHNICAL FIELD

The invention relates to a filter device that can be placed via a catheter delivery system in a vessel of a mammalian body to reduce the risk of embolisms. If needed, such filter can be removed from the vessel of a mammalian body without causing traumatic damage to the vessel of a mammalian body. The invention further relates to features that facilitate retrieval and prevent migration of the filter.

BACKGROUND ART

Inferior vena cava filters, also called IVC filters or Greenfield filters, are medical devices that are implanted into the inferior vena cava to prevent pulmonary emboli. They work by trapping emboli while still permitting the flow of blood, thereby preventing an embolus from sealing off a vessel. IVC filters are used if anticoagulation is ineffective or contraindicated.

IVC filters are inserted via the blood vessels (i.e., placed endovascularly). Known filters can be compressed into thin catheters permitting access to the venous system via the femoral vein or the internal jugular vein. A catheter is guided into the IVC using fluoroscopic guidance. The filter is pushed through the catheter and deployed into the desired location. IVC filters are usually positioned just below the junction of the IVC and the lowest renal vein.

IVC filters may be permanent or retrievable. Retrievable filters have a configuration that allows them to be pulled back into a catheter or sheath to be removed. In either case, these filters also include structure to anchor the filter in place within the vena cava. Typical features include elongate diverging anchor elements called second extension elements. These frequently have hooked ends that penetrate the vessel wall to prevent migration within and along the vessel. Some types of filters also have first extension elements which contact the wall of the vessel at a point that is axially displaced from the point of contact by the second extension elements. This apposition helps to keep the filter axially oriented (i.e., prevents tipping) and centered.

US Patent Publication No. 2003/0060843 shows a filter which has an umbrella-like structure to capture emboli with struts that connect the filter to a catheter which has a capsule on its end to hold the filter in a collapsed configuration. The catheter and capsule remain in place while the filter is in use so no vessel wall-holding features are required. The filter readily collapses as it is drawn into the capsule since there are no extensions to get in the way.

U.S. Pat. No. 6,793,665 and US Patent Publication No. 2005/0080447 show a filter with one or more meandering filaments that define a self-expanding structure that can be drawn into a catheter. The pressure of the meandering filament(s) against the vessel wall prevents the filter from migrating. In one embodiment, the filter is symmetrical and can be placed through a jugular or femoral access.

US Patent Publication No. 2005/0288703 shows a filter with a capture part with obliquely extending struts stemming from a hub which is attached at the strut endpoints to a series of V-shaped extensions that are displaced in a flow direction from the ends of the struts. The ends of the extensions have sharp tips that engage the vessel wall to prevent movement.

US Patent Publication No. 2006/0041271 shows a filter with a cover that can be placed through a catheter. The filter is self-expanding from a compressed shape that is assumed by it when it is inside the catheter. A cover over those portions of the filter that would otherwise contact the vessel wall reduces pressure on the wall. The cover also helps to resist incorporation of the filter into the vessel wall by endothelialization. Oppositely-directed tips engage the wall to prevent movement.

U.S. Pat. No. 5,370,657 shows a filter in which two self-expanding corolla elements are interlaced in opposite directions. At the center of each corolla is a hook that can be approached from opposite ends by loops that engage each hook to pull the corollas apart. The corollas are held together by a resilient element that breaks when the two corollas are pulled apart, allowing each corolla to be drawn into, and collapsed within, a sheath for retrieval.

U.S. Pat. Nos. 5,836,969 and 6,126,673 show a filter with multiple corollas that can assume a very small size when compressed within a catheter before deploying. The filter is made of filter-wires that extend generally upstream from a central region of connection, free ends that engage the vessel wall.

U.S. Pat. Nos. 6,273,901 and 6,589,266 show a filter that is similar that of U.S. Pat. No. 5,370,657, but the wires making up the corollas follow much more complex trajectories. Also, an embodiment with hooks on the corolla hubs is shown, but they are not explained in the patent.

U.S. Pat. No. 7,018,401 shows a filter with oppositely-directed dome portions that can have hooks at the tops of their domes. The patent says the hooks can be used for retrieval. The domes are flexible.

There is a need in the art for vena cava filters with features that make them easy to withdraw while satisfying the various practical constraints of manufacturability, ease of use, reliability, cost and so forth.

DISCLOSURE OF INVENTION

A recoverable embolus filter has a symmetrical design with two corollas with radially extending extensions that are mutually interconnected to permit them to slide with respect to each other. The symmetry of the filter allows it to be delivered without concern for orientation, which, for example, allows the same filter, stored in a catheter, to be delivered through either a femoral or jugular access. The corollas collapse by pulling them apart. The filter can be retrieved by approaching the filter from opposite ends and snagging the respective corollas to pull them apart. The collapsed filter can then be drawn by pulling one of the ends of the collapsed configuration into a recovery sheath.

According to an embodiment, an embolus filter has a first corolla having a first axis and first extension elements connected at a first hub. The first extension elements extend from the first hub radially away from the first axis and longitudinally along the first axis in a first axial direction. A second corolla has a second axis and second extension elements connected at a second hub. The second extension elements extend from the second hub radially away from the second axis and longitudinally along the second axis in a second axial direction. The first and second axes are collinear with the corollas and oriented such that the first and second directions are mutually opposite. Connectors slidably linking one or more pairs of the extension elements, with each pair including one of the first extension elements and one of the second extension elements.

In a variation of the foregoing embodiment, the connectors include cylindrical tubes. Preferably, each of the first and second extension elements has an engagement element to engage the wall of a blood vessel. The engagement element may be, for example, a hook shaped to point radially away from a respective one of the first and second axes. At least some of the first and second extension elements preferably have engagement elements at their ends remote from their respective ones of the first and second hubs. The first hub preferably has a first hook extending in a direction opposite the first direction and the second hub preferably has a second hook extending in a direction opposite the second direction. Preferably, the first and second corollas are movable with respect to each other such that the first and second hubs can be pushed together or pulled apart.

According to another embodiment, an embolus filter has a first corolla having a first axis and first extension elements connected at a first hub, the first extension elements extending from the first hub radially away from the first axis and longitudinally along the first axis in a first axial direction. A second corolla has a second axis and second extension elements connected at a second hub. The second extension elements extend from the second hub radially away from the second axis and longitudinally along the second axis in a second axial direction. The first and second axes are collinear with the corollas and oriented such that the first and second directions are mutually opposite. Each of the first extension elements is connected to one of the second extension elements.

In a variation of the foregoing embodiment, the first and second extension elements are interconnected by cylindrical tubes. Each of at least some of the first and second extension elements has an engagement element. Each of the engagement elements may include a hook which is shaped to point radially away from a respective one of the first and second axes.

In further embodiments, preferably, each of at least some of the first and second extension elements has an engagement element at their ends remote from their respective ones of the first and second hubs. Preferably, the first hub has a first hook extending in a direction opposite the first direction and the second hub has a second hook extending in a direction opposite the second direction. Preferably, the first and second corollas are movably interconnected. The first and second corollas are preferably slidingly interconnected. Also, preferably, the first and second corollas are movable with respect to each other such that the first and second hubs can be pushed together or pulled apart. The connections between the respective ones of the first and second extension elements may be the sole interconnection between the first and second corollas.

According to yet another embodiment, an embolus filter has first and second corollas, each of the corollas having extension elements extending radially away from a common axis. The extension elements of the first corolla extend along the common axis in a first direction and the extension elements of the second corolla extend along the common axis in a second direction opposite the first. The corollas are slidingly interconnected such that the extension elements are free to move radially and such that the corollas can be pushed together and pulled apart while remaining interconnected.

In a variation of the foregoing embodiment, the first and second corollas are slidingly interconnected by their extension elements. Preferably, the first and second corollas are slidingly interconnected by tubes connecting the extension elements of the first and second corollas in pairs. Also, preferably, at least some of the first and second corolla extension elements have an engagement element at an end thereof. One or more of the engagement elements may include a hook shaped to point radially away from a respective one of the first and second axes. At least some of the first and second extension elements can have engagement elements at their ends remote from their respective ones of the first and second hubs. Preferably, the first and second corollas have first and second hubs, respectively, the first hub having a first hook extending in a direction opposite the first direction and the second hub having a second hook extending in a direction opposite the second direction.

According to another embodiment, a method of retrieving an embolus filter includes grasping, from opposite directions, two slidingly interconnected filter elements or components within a vessel wall, each of the filter elements having engagement elements positioned in a circumferential pattern about a mutual longitudinal axis and in engagement with the vessel wall; pulling the two filter elements apart such that the force of pulling apart is redirected to draw engagement elements of the filter elements toward the mutual longitudinal axis. Preferably, the method also includes pulling the two filter elements into a retrieval sheath extending along the vessel wall. Alternatively, the method of retrieval can provide for restraining one of the filter components and sliding the other filter component relative to the restrained filter component so as to radially collapse or draw inwardly the extension elements. Preferably, the method provides for sliding, within a connector, the extension elements of the sliding component relative to the extension elements of the restrained component. The sliding further preferably includes sliding the connector relative to the extension elements of the restrained component such that the components of the filter are spaced apart and the engagements elements are sufficiently radially collapsed so that the filter can be withdrawn into a sheath.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

MODE(S) FOR CARRYING OUT THE INVENTION

Figure 1A:
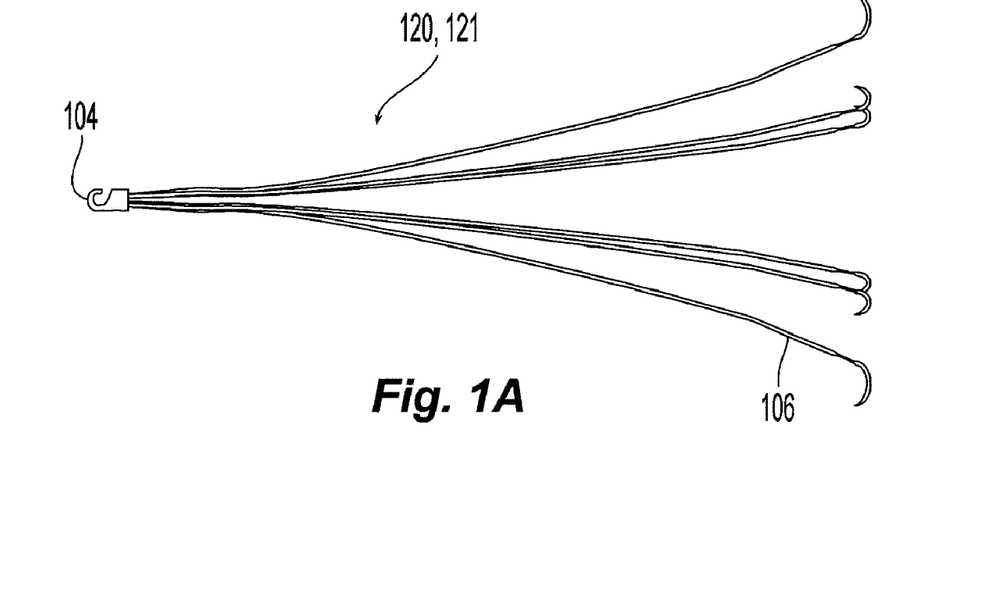
FIGS. 1A and 1B show side and end views of a corolla component of a symmetrical embolus filter.
Figure 1B:
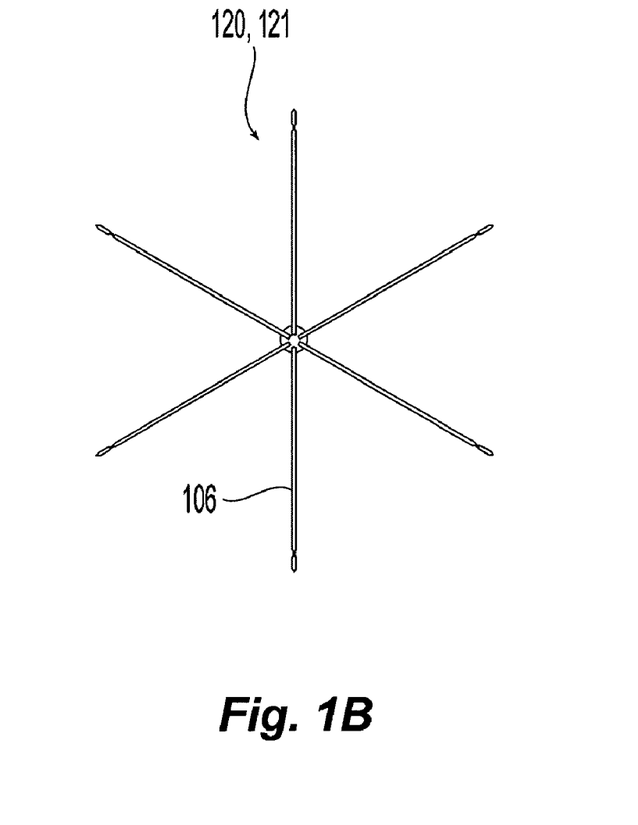
Figure 2A:
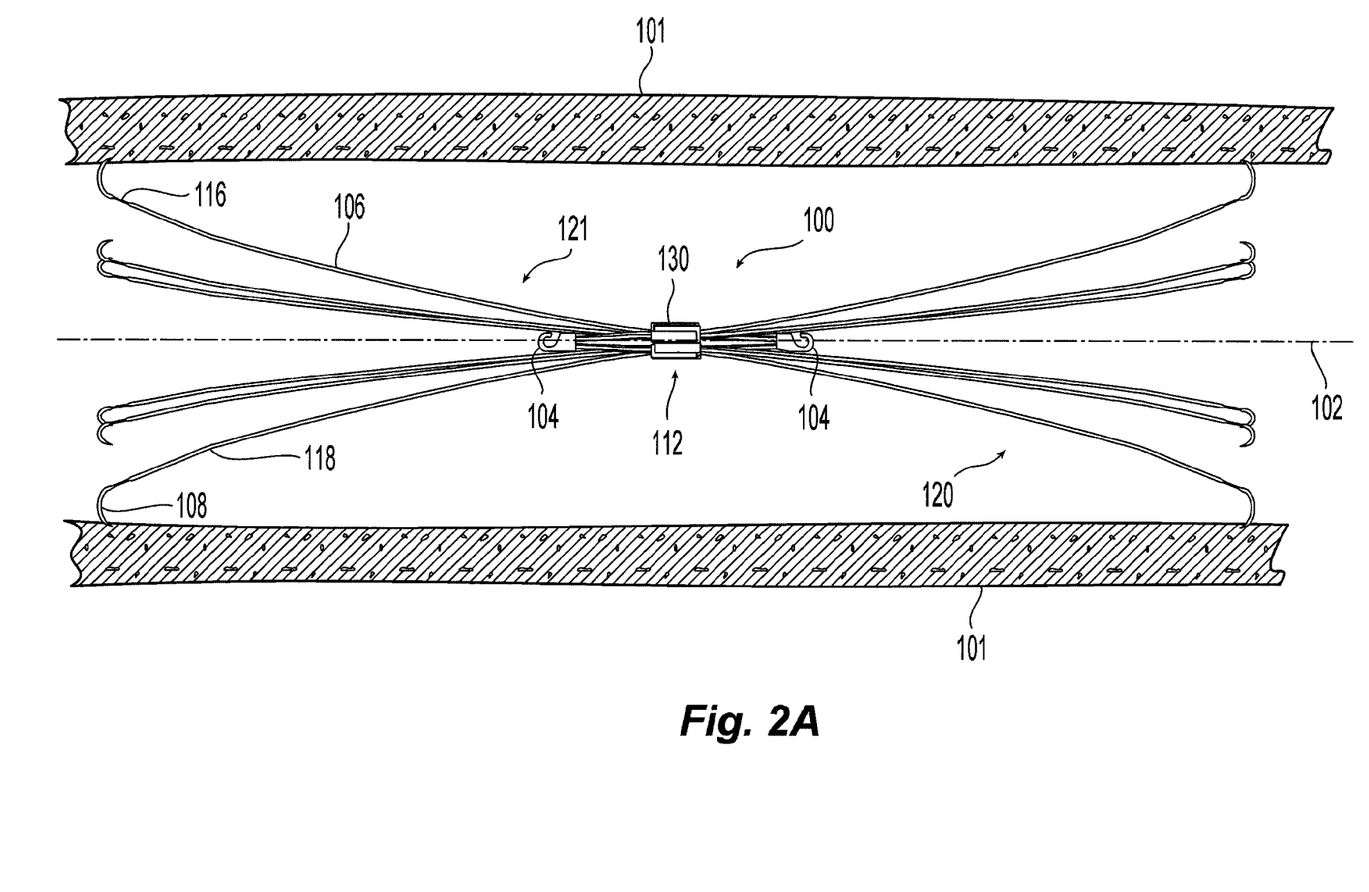
FIG. 2A shows the symmetrical embolus filter in a deployed state.

Referring to FIGS. 1A, 1B, and 2A, an embolus filter 100 has two oppositely oriented components, preferably configured as corollas 120 and 121 each made up of extension elements 106 that stem from a respective hub 104. FIGS. 1A and 1B show the configuration of the corollas 120, 121 as viewed from the side and as viewed from the end. In FIGS. 1A and 1B, a single corolla 120, 121 is shown, the corollas 120 and 121 being identical. In the filter 100, the extension elements 106 are passed through a connector 130 preferably formed by an array or cluster of tubes with one or more pairs of extension elements 106 per tube 130. The tubes 130 are preferably circular cylindrical, but other tubular geometries are possible as described further herein. Each pair of extension elements 106 disposed within a tube 130 includes at least one extension element 106 from each of the two opposing corollas 120 and 121 such that the two corollas 120 and 121 are linked together. The extension elements 106 are free to slide in the tubes 130 thus slidably connecting the opposing corollas 120 and 121. Thus, the two corollas 120 and 121 can be drawn apart or pushed together while remaining interconnected.

The tubes 130 of the connector array are preferably separate from one another so that the extension elements 106 can spread the tubes apart or draw them together as can be seen by comparing the series of figures: FIGS. 3B to 3D. More specifically, the tubes 130 are expanded radially outward or drawn in radially inward relative to the filter axis 102 in response to the co-directional and counter directional forces generated by the relative movement between the extension element pairs 106 within the individual tubes. As described in greater detail below, the direction and magnitude of the forces acting on a tube 130 is dependent upon the location of the tube along each extension element in the pair and the shape of the individual extension elements. Thus for example, when a tube 130 is located at the midpoint of each of the extension elements 106, the tube is preferably biased radially outward from the filter axis 102, as seen in FIG. 3D. Moreover, when the hubs 104 are axially spaced such that the tube 130 is at the distal ends of the oppositely directed extension elements 106, the extension elements 106 are drawn radially inward under tension so as to bias the tubes 130 radially inward toward the filter axis 102, as seen for example in FIG. 3E.

Preferably, at least some of the extension elements 106 have hooks 108 at their ends to engage the wall of a blood vessel 101. Engagement devices other than hooks can be used to limit the movement of the filter 100. Moreover, the extension elements can also have one or more bends, such as indicated at 118 or be smoothly curved over substantially its entire length. Preferably, engagement devices such as the hooks 108 are provided on each of the opposing corollas 120 and 121 such that axial movement in both directions within a blood vessel is limited. Where a very secure engagement mechanism, such as the hooks 108, are used to limit movement of the filter 100, preferably, the extension elements 106 are further supported or configured so as to limit the amount of traction force that can be transmitted to the vessel wall 101 through the extension element 106 by the hook 108 or other engagement mechanism. The support further limits the trauma due to deployment or recovery, and any other time the filter 100 may be subjected to forces tending to move it. For example, as disclosed in U.S. Pat. No. 6,258,026 for "Removable embolus blood clot filter and filter delivery unit," which is incorporated by reference in its entirety, hooks 108 (or other engagement elements) can be supported by weakened portions 116 which bend when a predefined force is applied to it, thereby permitting the hook 108 (or engagement element) to withdraw or at least reduce its ability to transmit traction.

The extension elements 106 are preferably made from shape memory wire, for example, Nitinol, but they can also be made from any other suitable materials. The extension elements 106 can be held in the hubs 104 by a forged press-fit, a weld, adhesive, or a mechanical fastening feature such as mating male and female threaded parts on the hubs 104 and the respective extensions elements 106.

Figure 2B:
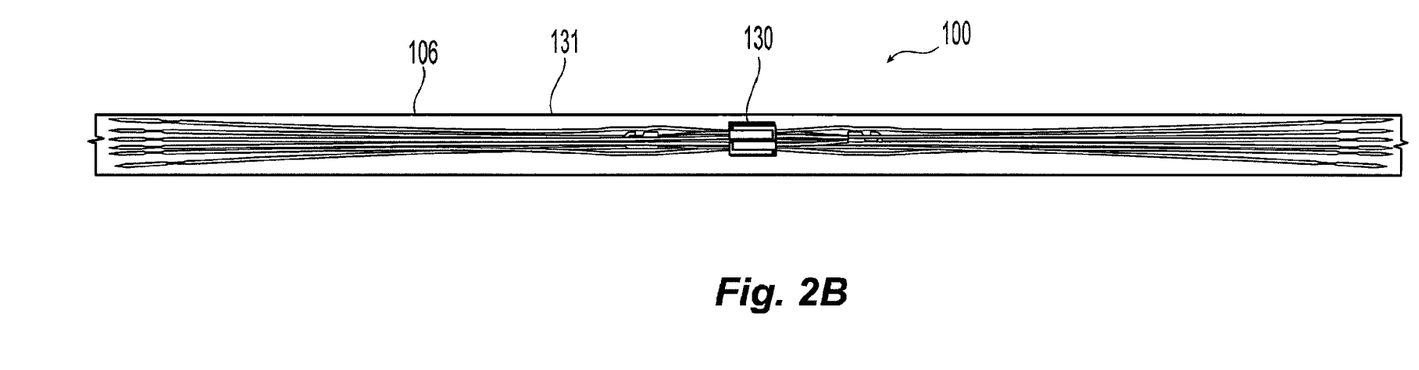
FIGS. 2B and 2C show the deployment configuration of the filter of FIG. 2A.
Figure 2C:
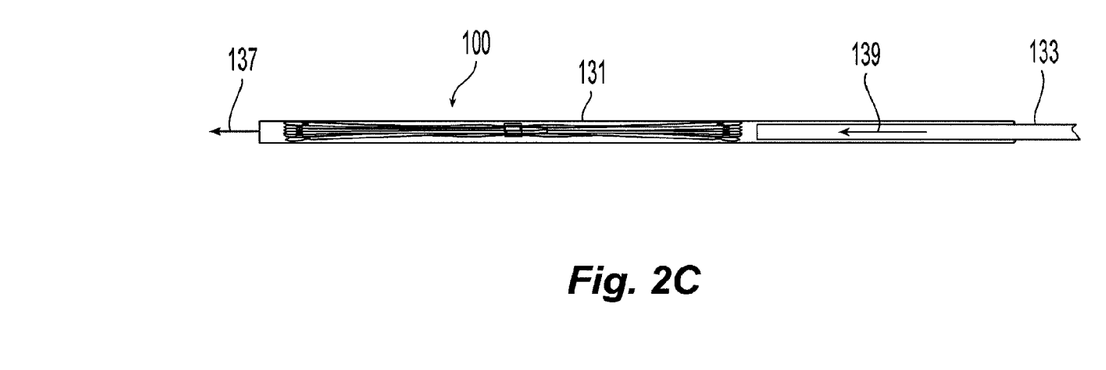

To prepare the filter 100 for deployment, the two corollas 120 and 121 may be pushed together to form the deployed configuration shown in FIGS. 2B and 2C. The collapsed filter 100 shown in FIG. 2B is held in a catheter 131 and pushed out by a pushing shaft 133 in the direction indicated by arrows 137 and 139. The hooks 108 can be straightened by holding a shape memory alloy of which they are made at a predetermined temperature. This can be done, for example, by flushing or circulating saline at a predefined temperature until deployed, to transition the material between the austenite and martensite phases according to known methods for articles made of shape memory and as discussed in the patent incorporated by reference above.

Figure 3A:
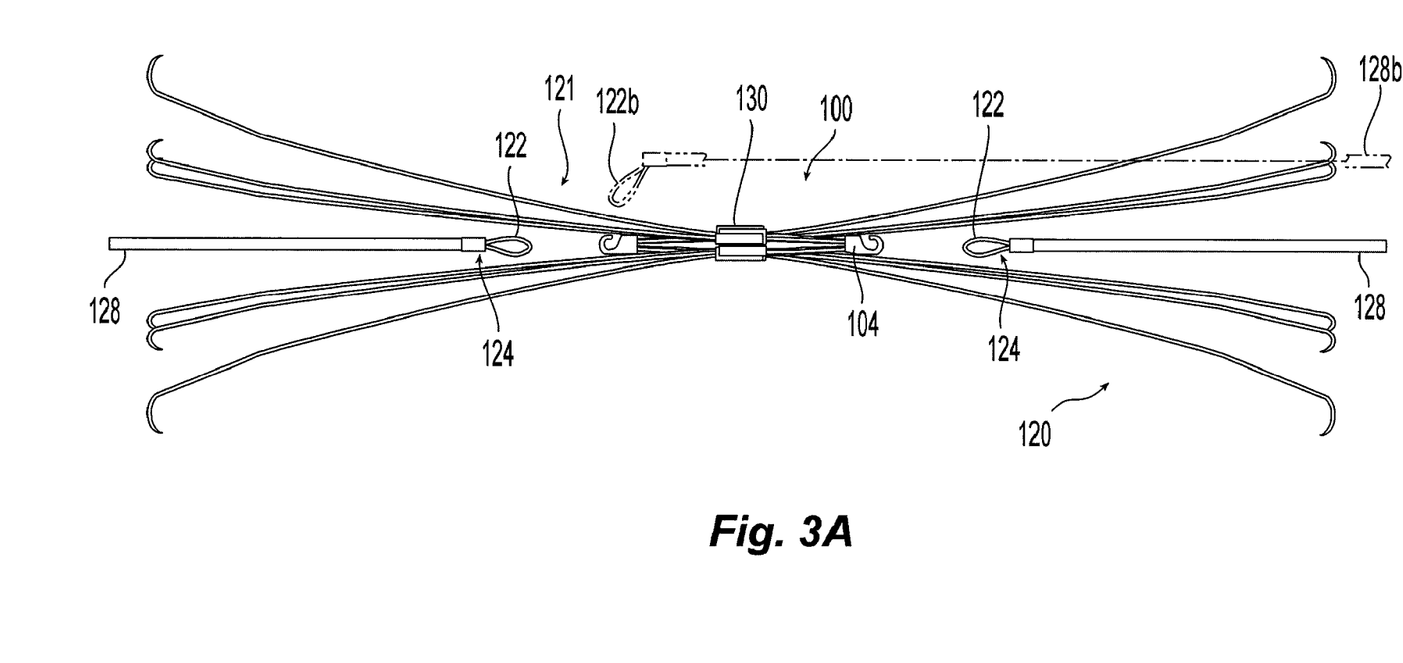
FIGS. 3A to 3F illustrate the filter of FIG. 2A in various stages of a retrieval operation.
Figure 3B:
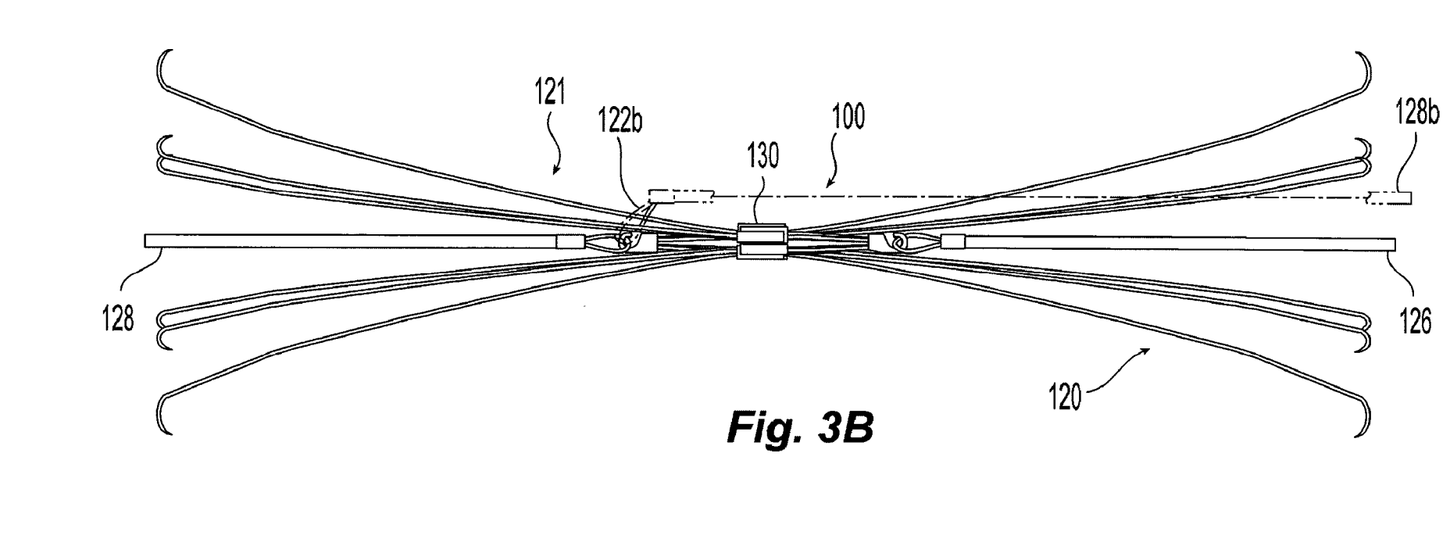
Figure 3C:
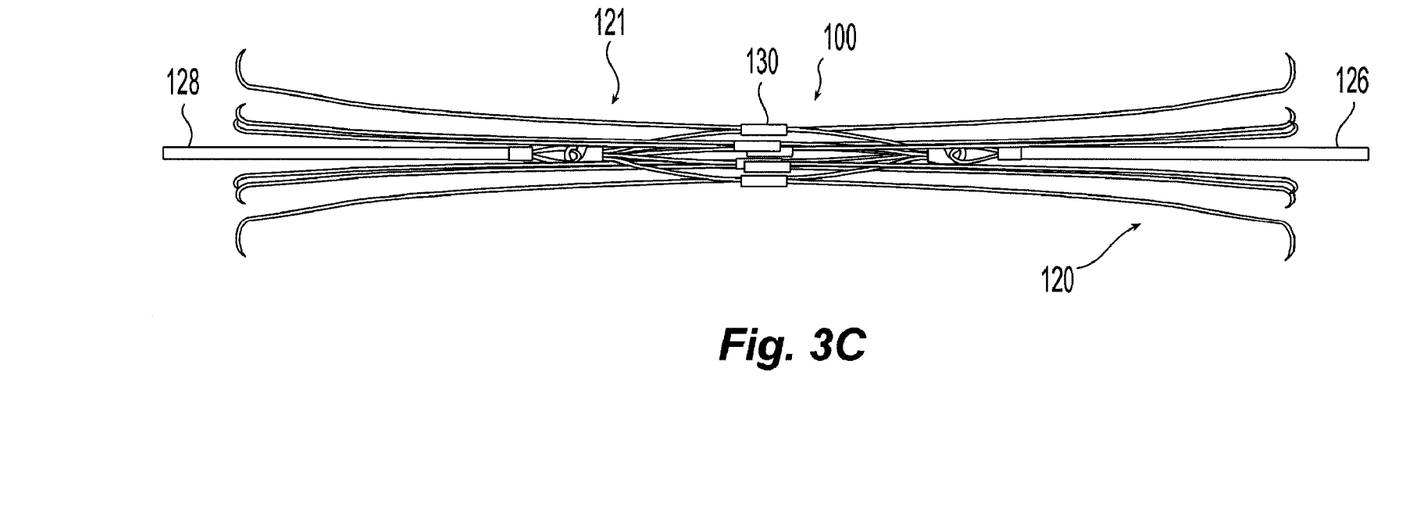
Figure 3D:
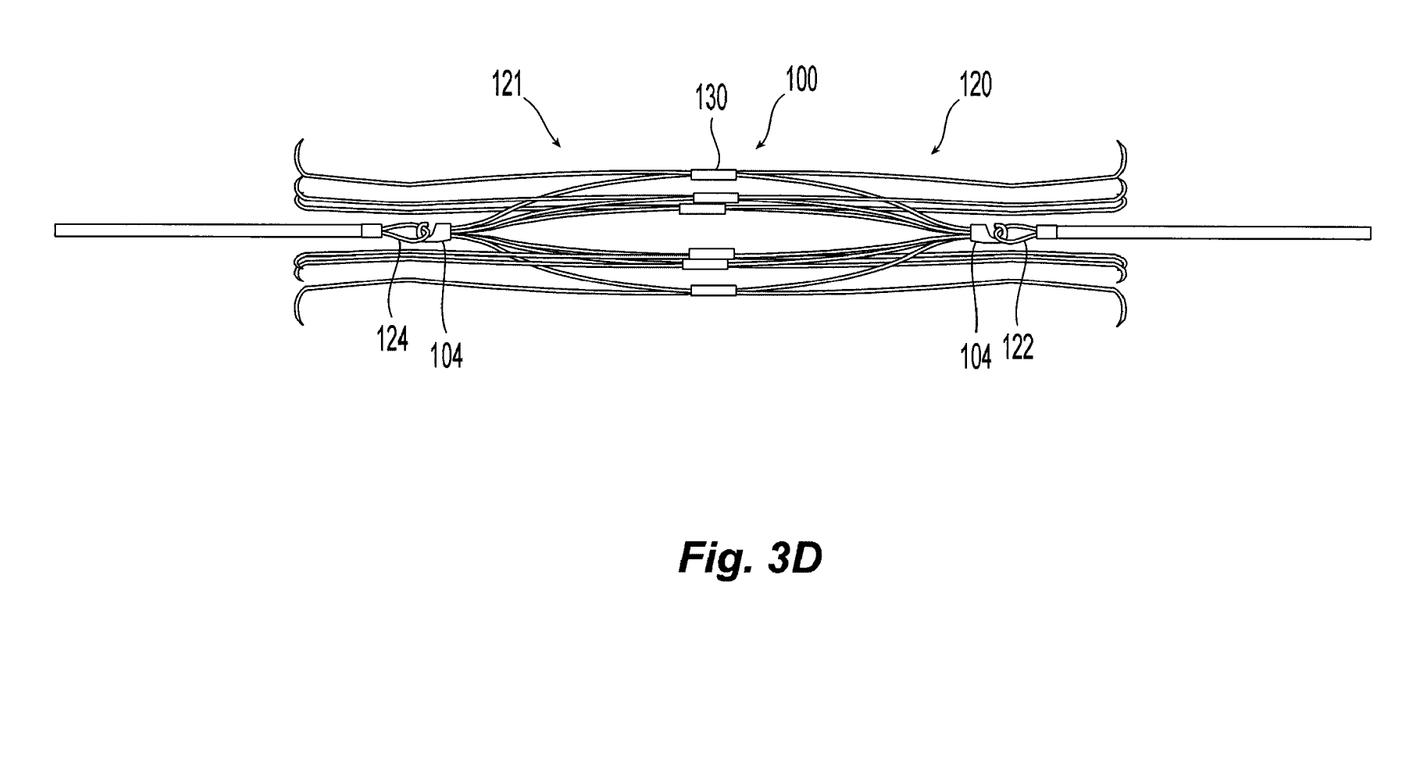
Figure 3E:
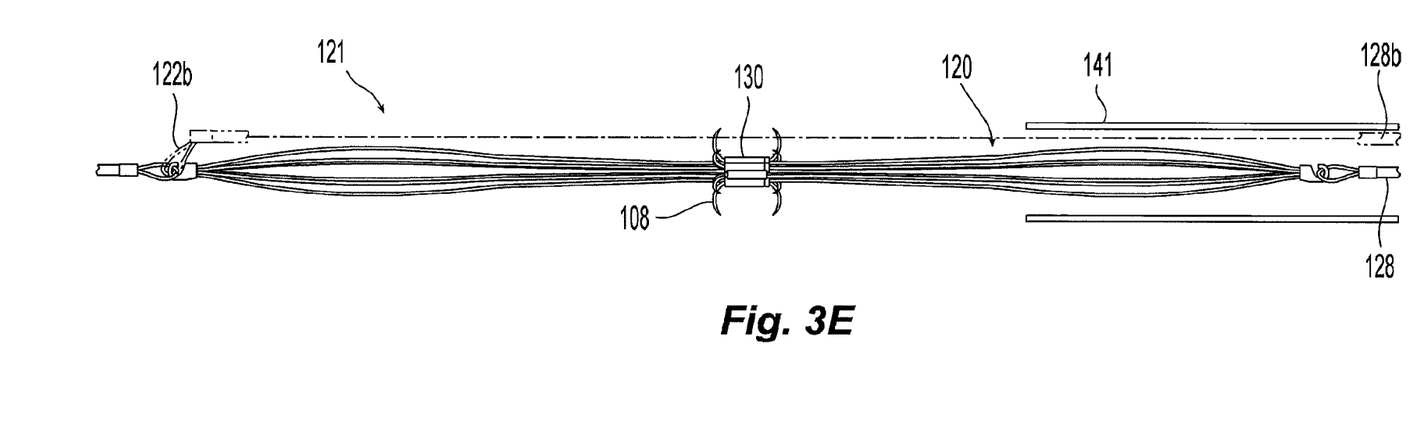
Figure 3F:
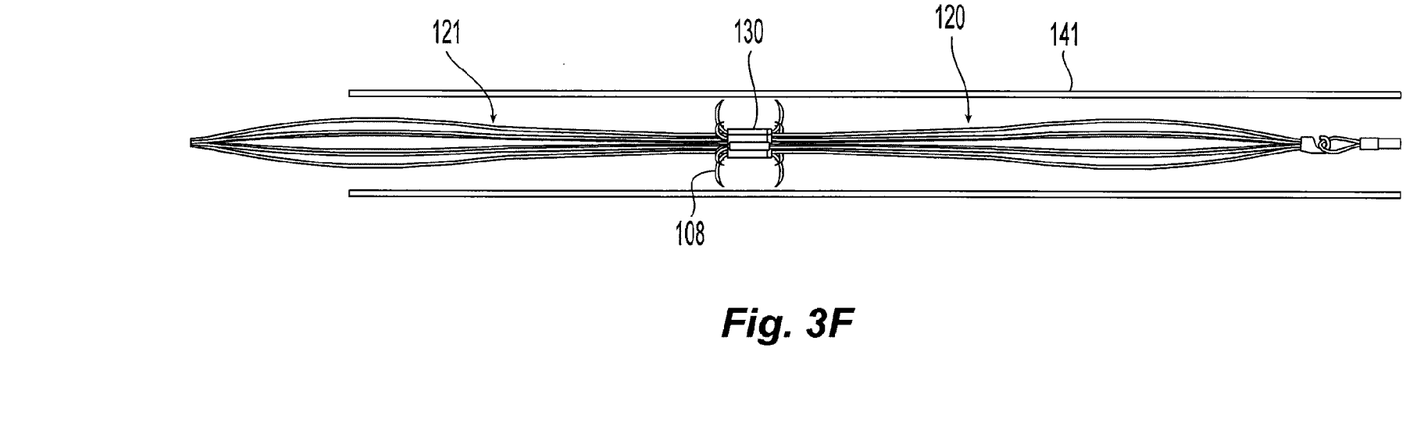

Referring to FIGS. 3A to 3F, to recover the filter 100, the hubs 104 are pulled apart until the corollas 120 and 121 are held together at the ends of the extension elements 106 as shown in FIGS. 3E and 3F. The resulting configuration has a small cross section and permits the filter 100 to be pulled into a recovery catheter 141. The hubs 103 can be pulled apart by any suitable means, for example, by providing hooks on the opposite hubs 104 which can be caught by a device or tool such as, for example, a catheter 128 with a loop 122 at its end. More specifically, the hubs 104 preferably include a hook portion which can be engaged by the catheter 128. The hook portions are preferably oppositely directed such that the hook portion for one corolla 121 extends distally and the hook portion of the other corolla 120 extends proximally. Catheters 128 can be brought into position as shown in FIG. 3A by inserting in jugular and femoral accesses, respectively and looped around the hub 104 hooks. The catheters 128 preferably have markers to allow their tips 124 to be located using radiological imaging. The loops 122 are engaged with the hubs 104 as shown in FIG. 3B and gradually pulled apart as shown in the series of Figures from FIGS. 3C to 3E. This causes the extension elements 106 to be pulled through the tubes 130. The tubes 130, which are not interconnected, are free to spread apart, for example as shown in FIG. 3D.

In an alternative method of retrieving the embolus filter 100 disposed substantially along the blood vessel axis, as shown for example in FIG. 2A, the extension elements 106 of one the two corollas 120, 121 is restrained and the opposing extension elements 106 of the other corolla are pulled axially so as to collapse the filter 100 for retrieval. The alternate method is shown schematically in FIGS. 3A and 3B. A device or tool, preferably another catheter 128*b*, shown alternatively in phantom, approaches and engages one corolla 121 preferably at the hook portion of the hub 104 with its loop 122 so as to restrain the component from any further axial movement. Another catheter 128 approaches and engages the hook portion of the hub in the opposing corolla 120 with its loop 122. The device 128 axially pulls or draws the corolla 120 such that the extension elements 106 of the corolla 120 slide past the extension elements of the restrained corolla 121 within the connector or tube array 130. In order to effectively restrain the one corolla 120 while pulling on the other, the device 128*b* is of a sufficient stiffness to avoid buckling under the pulling force. Now referring to FIG. 3E, the device 128 continues to axially pull on the corolla 121 such that the engagement mechanism or hooks contact the connector 130 and slides the connector 130 distally along the extension elements 106 of the restrained corolla 121. As with the method described above, the connector is finally located at the distal ends of the extension elements 106, thereby collapsing the filter 100 for withdrawal into the sheath 141.

As is illustrated in the FIGS. 3A, 3B, and 3E, the alternate method provides for approaching of the filter from a single side, for example, the proximal corolla 120 of the filter 100. Accordingly, the method provides for retrieval of the filter 100 from a single access point, being one of the jugular and femoral access. Further in the alternative, the method can be performed from two access points such that, for example, restraining of the corolla 121 is performed from the jugular access and sliding of the other corolla 120 is performed from the femoral accesses.

Although in the illustrated embodiment, the corollas 120, 121 each have six extension elements 106, the numbers of extension elements may vary. In addition, the number of extension elements 106 in the corollas 120, 121 need not be identical. Also, the sizes of the extension elements 106, or the types of engagement elements (e.g., hooks 108) employed, may vary within a corolla 120,121 and between corollas 120, 121.

Figure 4A:
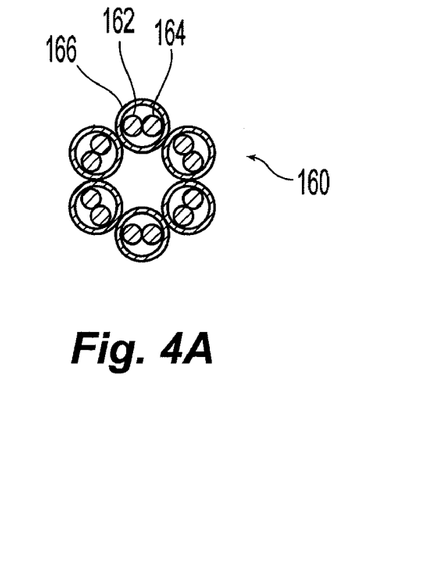
FIGS. 4A to 4D and 4F show different harnesses that can be used to make variations of the embodiment of FIG. 2A.

Referring now to FIG. 4A, an array of tubes 164 for use in filter 100 carries oppositely-directed extension elements 162 and 164 preferably in pairs, as described above. In an alternative embodiment, the tubes 166 are affixed together to form a single unit 160. In this configuration, when the corollas 120, 121 are drawn apart, the extension elements 106 are held close together. It may be desirable for the extension elements 106 to have an alternative shape which can minimize or otherwise eliminate the elements 106 from crossing one another. For example, the extension elements 106 may be substantially straight over most of their lengths as the extension element 175 in FIG. 4E. This is because the curved shape of the extension elements 106, with the concavity facing the axis in the deployed position of FIG. 2A, can cause the ends of the extension elements 106 to move toward, and cross, the axis 102 (see FIG. 2A) and further possibly cross one another. With straight extension elements 175, using a single piece tube array as the single unit 160, the extension elements 175 will move progressively toward the axis 102 without crossing each other.

Figure 4B:
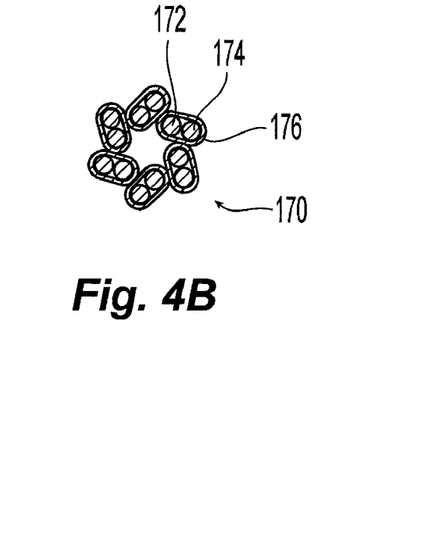
Figure 4C:
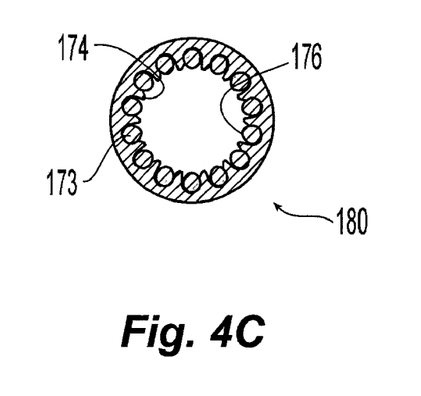

FIG. 4B shows another embodiment of a tube array 170 for use in filter 100 in which the tubes 176 are oval-shaped and arranged to pack them close together. Each tube 176 in the array 170 preferably carries a pair of oppositely-directed extension elements 172 and 174 as in the previous embodiments. The tubes 176 in this embodiment may be affixed to each other or independently movable. FIG. 4C shows a single toothed element 180 that holds the oppositely-directed extension elements 174 and 176 adjacent each other, but without confining them to pairs within tubes. The spring tension in the extension elements 174, 176 may be sufficient to bias the elements radially outwardly so as to keep the extension elements 174 and 176 within the slots or channels 173.

Figure 4D:
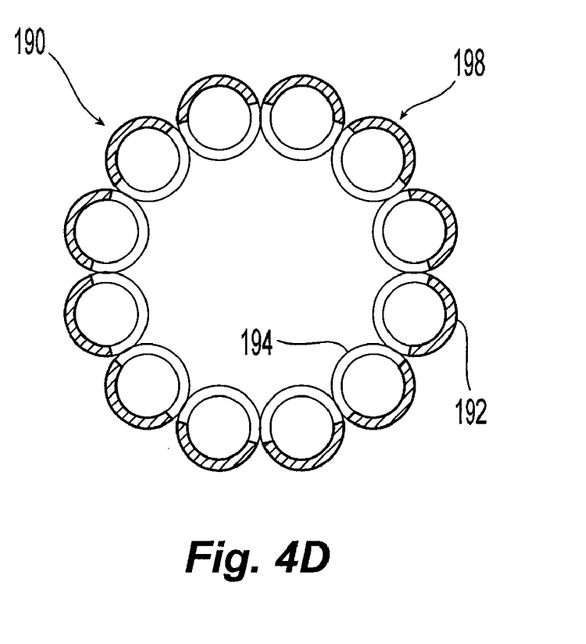
Figure 4E:
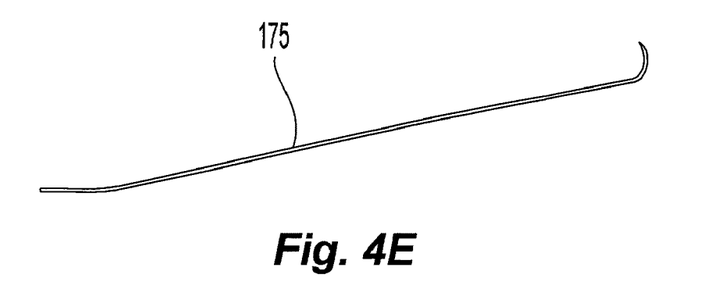
FIG. 4E shows an extension element for use with an embodiment of a filter similar to the design of FIG. 2A.
Figure 4F:
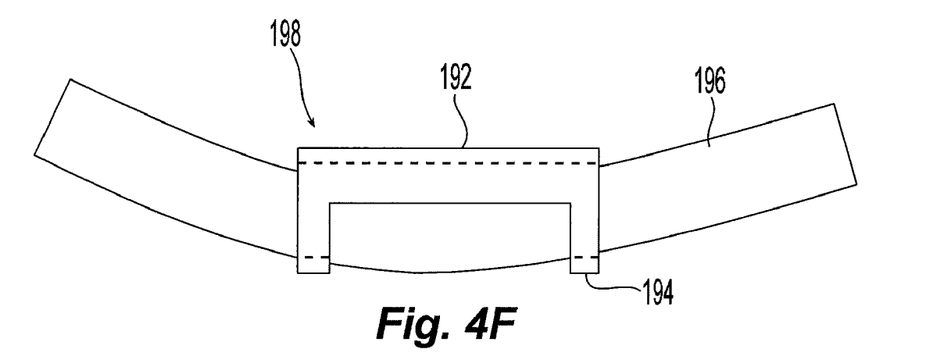

FIGS. 4D show a preferably substantially circular array 190 of tubes 198 enclosing an interior space. Each of the tubes 198 may carry a single extension element 196 (See FIG. 4F). This embodiment differs from the foregoing in that the tubes 198 carry only one extension element 196 each. Moreover, the tubes 198 are preferably affixed to each other form the array 190. Each tube 198 is preferably substantially circular cylindrical with has an opening 194 facing the center or in communication with the interior space of the array 190. The closed side 192 or wall of the tube 198 preferably faces radially the exterior space away from the array 190. The openings 194 permit sharply curved extension elements 196 to pass through the tubes 198 with lower friction. Thus, the tubes 198 do not need to be enlarged to provide additional tolerance to accommodate the bend. This, in turn, helps to keep the size of the array 190 small. Note that they array structure of 190 can be constructed with tubes 198 having a substantially continuous wall or no radial opening. Further in the alternative, tubes 198 can be constructed two or more rings that are spaced apart axially through which the extension elements 196 can pass.

Figure 5A:
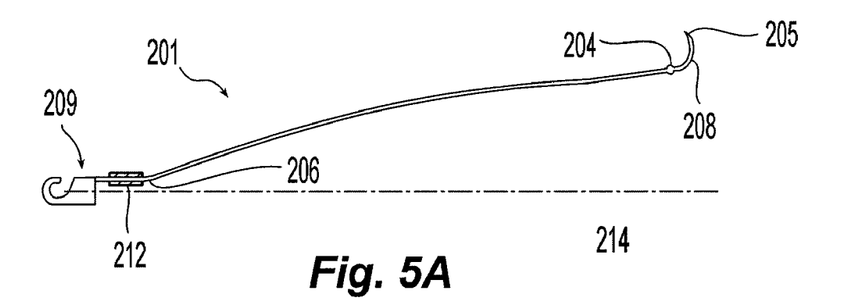
FIGS. 5A and 5B illustrate features of various embodiments of an embolus filter.
Figure 5B:
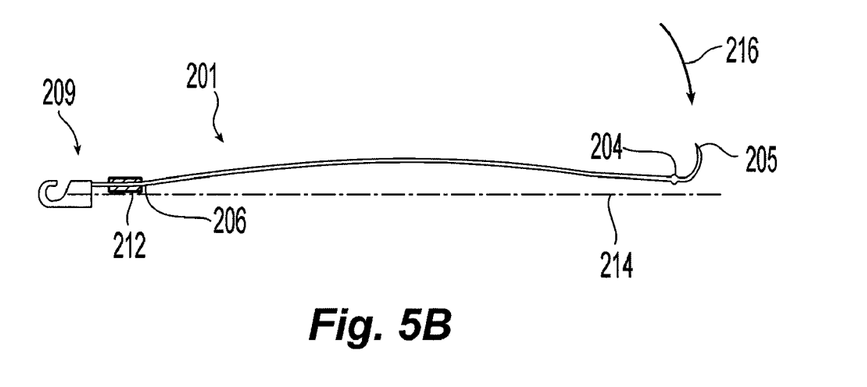

Referring to FIGS. 5A and 5B, stops 204 may be provided on the extension elements 201 to prevent the ends 205 from sliding out of the tubes 212. The stops 204 can be separate portions welded to the extension elements 201 or otherwise affixed to the extension elements, or they can be integral parts of the extension elements 201.

FIGS. 5A and 5B also illustrate how a sharp bend 206 provided near the hub 209 can cause the hook 205 to be pulled radially inward as shown by arrow 216 during the initial displacement of a tube 212 over the bend 206. In this way, the hook 205 need not be dragged along the blood vessel wall as the corollas are drawn apart.

FIGS. 5A and 5B also illustrate another feature which may minimize or eliminate the extension elements 201 crossing one another while still permitting them to slide within the tubes 212 in a fixed array (not shown in the present figures). The tube 212 is assumed to be one member in an array and have an inner diameter that is larger than the extension element 201 outer diameter. As a result, when the extension element 201 is drawn through the tube 212, the sharp bend 206 is not completely straightened. Because the sharp bend 206 is not completely straightened, the end 205 swings toward the axis 214 without crossing it, and thus, the extension elements 201 avoid crossing one another upon being radially drawn inward. In addition, the extension elements 201 may be curved so as to avoid the ends 205 from crossing the axis 214.

The extension elements of the various embodiments can be held together by means other than tubes as shown by, for example, the embodiment of FIG. 4C. Also, the extension elements can pass through tubes or channels individually, in pairs as shown in FIG. 4A, individually as shown in FIG. 4C, or in a larger number per channel or tube (not shown).

Figure 6A:
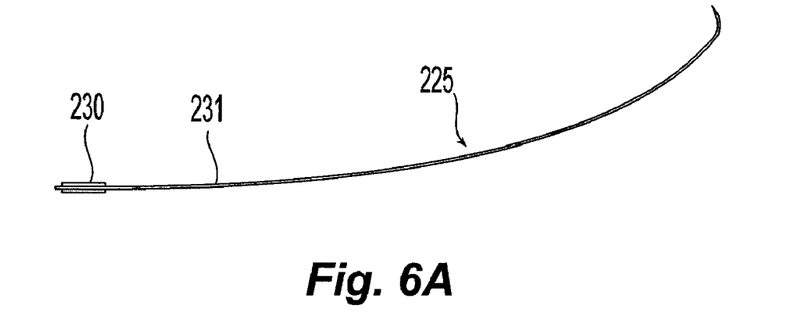
FIGS. 6A to 6C illustrate embodiments that provide for predictable sliding of extension elements with respect to linkages that interconnect them.
Figure 6B:
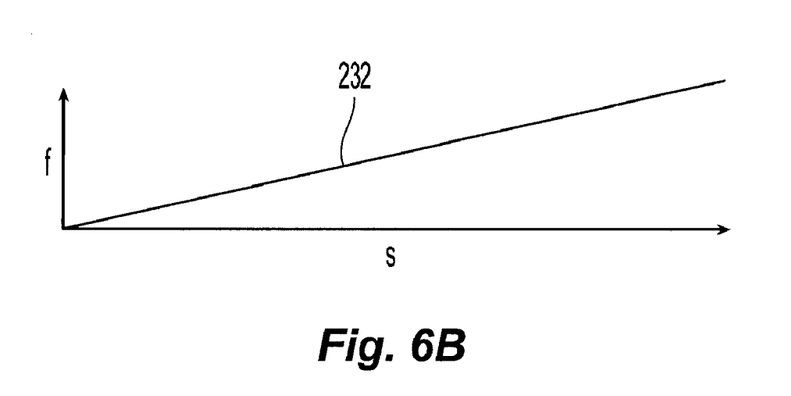

FIG. 6A shows another extension element 231 with a spiral curve shape over a major portion 225 thereof. As the extension element 231 slides relative to the tube 230, it will be observed that the curvature of the extension element 231 within the tube gradually increases as indicated in FIG. 6B which shows the frictional force (f, vertical axis) between the tube 230 and the extension element 231 versus displacement along the extension element 231 (s, horizontal axis). The progressive increase in force can help to keep tubes 230 centered between the two corollas as the corollas are drawn apart because each succeeding incremental displacement takes an increasing amount of force relative to the preceding incremental displacement of the tube 230 along the extension element 231 length. As a result, the tube 230 will not ride along the length of one extension element 231 while it remains at the hub end of the extension element with which it is paired because the frictional forces would be unbalanced between extension elements.

Figure 6C:
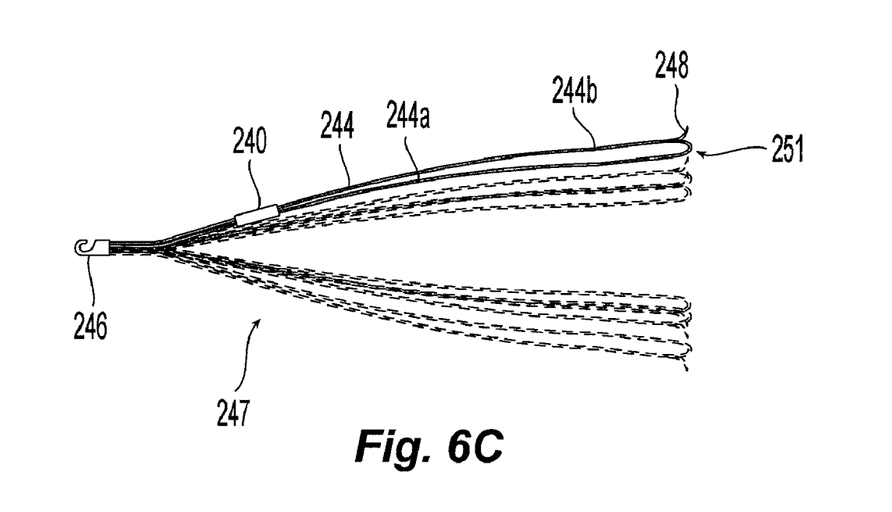

FIG. 6C shows another extension element 244 shape that generates a progressive frictional force relative to a tube 240. The extension elements 244 in this embodiment are loop-shaped structures preferably formed by a first run structure 244a and a second run structure 244b having a loop connecting the runs in between at the distal end. The extension elements 244 preferably include hooks 248 affixed at their ends and are interconnected by a hub 246 to form a corolla 247. As in previous embodiments, the tube 240 slides along each extension element 244 (only one tube 240 is shown, but there would be one for each extension element 244 and a pair of extension elements, one from each of two oppositely-directed corollas 247, in each tube 240). In this case, the friction force increases because the tube 240 has to pull the two runs 244A and 244B together as the tube moves toward the end 251 of the extension element 251.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

The invention claimed is:

1. An embolus filter, comprising:
   a) a first corolla having a first axis and first extension elements connected at a first hub, the first extension elements extending from the first hub radially away from the first axis and longitudinally along the first axis in a first axial direction;
   b) a second corolla having a second axis and second extension elements connected at a second hub, the second extension elements extending from the second hub radially away from the second axis and longitudinally along the second axis in a second axial direction;
   c) the first and second axes being collinear with the corollas and oriented such that the first and second directions are mutually opposite;
   d) a plurality of connectors, each connector linking one of the first extension elements and one of the second extension elements, said connectors positioned in a circumferential pattern that holds at least a portion of the first and second extension elements in a circumferential pattern; and
   e) wherein the first and second extension elements are movably connected to the connectors such that the first and second hubs can be pushed together or pulled apart while the first and second extension elements are still connected to the connectors.

2. The filter of claim 1, wherein the connectors include cylindrical tubes.

3. The filter of claim 1, wherein at least some of the first and second extension elements have engagement elements.

4. The filter of claim 3, wherein each of the engagement elements includes a hook shaped to point radially away from a respective one of the first and second axes.

5. The filter of claim 1, wherein at least some of the first and second extension elements have engagement elements at their ends and spaced away from the hubs.

6. The filter of claim 1, wherein the first hub has a first hook extending in a direction opposite the first direction and the second hub has a second hook extending in a direction opposite the second direction.

7. The filter of claim 1, wherein the first and second corollas are slidably movable with respect to each other such that the first and second hubs can be pushed together or pulled apart and wherein the first and second extension elements slide with respect to the connectors.

8. An embolus filter, comprising:
   a) a first corolla having a first axis and first extension elements connected at a first hub, the first extension elements extending from the first hub radially away from the first axis and longitudinally along the first axis in a first axial direction;
   b) a second corolla having a second axis and second extension elements connected at a second hub, the second extension elements extending from the second hub radially away from the second axis and longitudinally along the second axis in a second axial direction;
   c) the first and second axes being collinear with the corollas and oriented such that the first and second directions are mutually opposite;
   d) a connector having channels that are receptive of said first and second extension elements, said channels positioned in a circumferential pattern and spaced radially from said collinear axes;
   e) each of the first extension elements being movably connected to the second extension elements with said connector; and
   f) wherein each said extension element contacts said connector.

9. The filter of claim 8, wherein the first and second extension elements are interconnected by cylindrical tubes of said connector.

10. The filter of claim 8, wherein at least some of the first and second extension elements have engagement elements.

11. The filter of claim 10, wherein each of the engagement elements includes a hook shaped to point radially away from a respective one of the first and second axes.

12. The filter of claim 8, wherein at least some of the first and second extension elements have engagement elements at their ends and spaced away from the hubs.

13. The filter of claim 8, wherein the first hub has a first hook extending in a direction opposite the first direction and the second hub has a second hook extending in a direction opposite the second direction.

14. The filter of claim 8, wherein the first and second corollas are slidingly interconnected at said connector.

15. The filter of claim 8, wherein the first and second corollas are movable with respect to each other such that the first and second hubs can be pushed together or pulled apart.

16. The filter of claim 8, where there are connections between the first and second extension elements that are an interconnection between the first and second corollas.

17. An embolus filter, comprising:
   a) first and second corollas, each of the first and second corollas respectively having first and second hubs and extension elements extending radially away from a common axis;
   b) the extension elements of the first corolla extending along the common axis in a first direction and the extension elements of the second corolla extending along the common axis in a second direction opposite the first direction;
   c) a connector that movably joins the corollas, said connector having multiple channels that are positioned in a circumferential pattern;
   d) the first and second corollas being slidingly interconnected to said connector such that the extension elements of the first and second corollas are free to move radially and such that the first and second corollas can be pushed together and pulled apart while remaining interconnected, wherein the extension elements of the first and second corollas slide within said channels: and
   e) wherein the radial position of the extension element changes in relation to the common central axis of the hubs as the hubs move toward or away from each other.

18. The filter of claim 17, wherein at least some of the extension elements have engagement elements of the first and second corollas at their ends remote from the first and second hubs.

19. The filter of claim 17, wherein the first and second corollas have first and second hubs, respectively, the first hub has a first hook extending in a direction opposite the first direction and the second hub has a second hook extending in a direction opposite the second direction.

* * * * *